US005756776A

United States Patent [19]
Bombardelli et al.

[11] Patent Number: 5,756,776
[45] Date of Patent: May 26, 1998

[54] SEMI-SYNTHETIC TAXANES WITH ANTI-TUMOURAL ACTIVITY

[75] Inventors: Ezio Bombardelli; Bruno Gabetta; Paolo De Bellis, all of Milan, Italy

[73] Assignee: Indena S.p.A., Milan, Italy

[21] Appl. No.: 505,924

[22] Filed: Jul. 24, 1995

[30] Foreign Application Priority Data

Jul. 26, 1994 [IT] Italy ................... MI94A1592
Jun. 19, 1995 [IT] Italy ................... RM95A0413

[51] Int. Cl.$^6$ ................... C07D 305/14
[52] U.S. Cl. ................... 549/510; 549/511; 514/449
[58] Field of Search ................... 549/510, 511; 514/449

[56] References Cited

U.S. PATENT DOCUMENTS

| | | | |
|---|---|---|---|
| 5,200,534 | 4/1993 | Rao | 549/510 |
| 5,399,726 | 3/1995 | Holton et al. | 549/510 |
| 5,608,102 | 3/1997 | Bourzat | 560/39 |

FOREIGN PATENT DOCUMENTS 2092705  1/1993  Canada.
0 400 971  12/1990  European Pat. Off..
WO 93/02067  2/1993  WIPO.

OTHER PUBLICATIONS

E. Didier et al., "Expeditious Semisynthesis of Docetaxel Using 2-Trichloromethyl-1,3-Oxazolidine as Side-Chain Protection," *Tetrahedron Letters*, vol. 35, No. 19 (1994), pp. 3063-3064.

E. Didier et al., "2-Monosubstituted-1,3-Oxazolidines as Improved Protective Groups of N-Boc-Phenylisoserine in Docetaxel Preparation," *Tetrahedron Letters*, vol. 35, No. 15 (1994) pp. 2349-2352.

Denis et al. J. Am. Chem. Soc., 110 (17), pp. 5917-5919, 1988.

*Primary Examiner*—Ba K. Trinh
*Attorney, Agent, or Firm*—Pennie & Edmonds

[57] ABSTRACT

The present invention relates to novel derivatives obtained by oxidation and the stereospecific reduction of 10-deacetylbaccatine III, and successive esterification with a variously substituted isoserine chain to prepare taxol analogues. The products of the invention have cytotoxic and anti-tumoural activities and, when suitably formulated, can be administered by injection and/or orally.

8 Claims, No Drawings

SEMI-SYNTHETIC TAXANES WITH ANTI-TUMOURAL ACTIVITY

TECHNICAL FIELD

The present invention relates to a series of taxane derivatives for use in applications in place of taxol when anti-tumoural activity is desired.

BACKGROUND ART

Diterpenes with taxane skeletons, and in particular taxol, are known to have an anti-tumoural action against numerous human tumours. However, the use of these drugs, particularly taxol, involves some drawbacks due to unwanted side effects. For this reason, and since these anti-tumoural treatments rapidly induce resistance, the development of new molecules whose use reduces the problems observed in clinical use is of interest.

SUMMARY OF THE INVENTION

The present invention relates to novel taxane-skeleton derivatives obtained by semisynthesis and having a powerful anti-tumoural activity. The derivatives of the invention have formula (1):

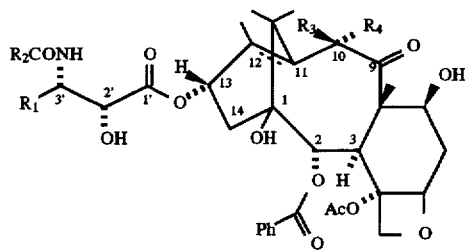

(1)

They can be divided into two series:

a) taxane derivatives containing a double olefinic bond at the 11,12-position and a hydroxy or acyloxy group at the 10α-position (taxanes of formula 1a)

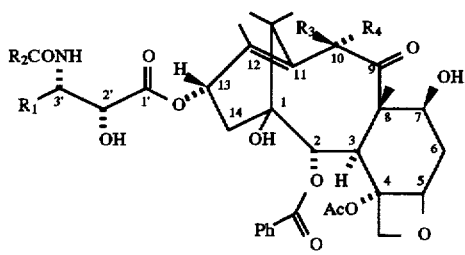

(1a) ($R_3$=H; $R_4$=OH or acyloxy)

(b) taxane derivatives containing a single bond between the carbon atoms in 11 and 12, the methyl in 12 being α-oriented, and a hydroxy or acyloxy group in position 10β (taxane of formula 1b)

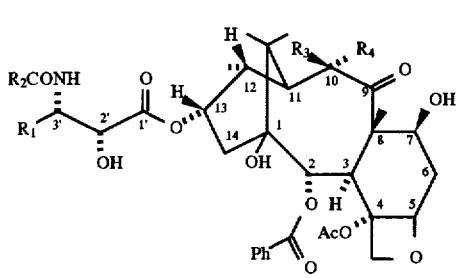

(1b) ($R_3$=OH or acyloxy; $R_4$=H)

DETAILED DESCRIPTION OF THE INVENTION

In taxanes of general formulae (1), (2), and (3), $R_1$ and $R_2$, which may be the same or different, can be $C_1$-$C_8$ alkyl, $C_2$-$C_8$ alkenyl, aryl (preferably phenyl) or heteroaryl group. $R_2$ can also be an alkoxy group having 1 to 8 carbon atoms and preferably a tert-butoxy group.

Although it is believed that any aryl or heteroaryl group is useful for $R_1$ and $R_2$, suitable aryl groups include phenyl and naphthyl, while suitable heteroaryl groups include heterocyclic groups having 5 or 6 members and containing one or more of N, O, or S as heteroatoms. $R_3$ or $R_4$ can be hydrogen, hydroxy, a $C_2$-$C_8$ acyloxy group or an alkoxy group having 1 to 8 carbon atoms. The dotted line between the carbon atoms 11 and 12 indicates the optional presence of a double bond.

In preferred compounds of formula (1a), $R_3$ is hydrogen and $R_4$ is a hydroxy, an alkoxy group having 1 to 8 carbon atoms or $C_2$-$C_8$ acyloxy group.

In, an alkoxy group having 1 to 8 carbon atoms compounds of formula (1b), $R_3$ is a hydroxy, an alkoxy group having 1 to 8 carbon atoms or $C_2$-$C_8$ acyloxy group and $R_4$ is hydrogen.

Taxanes of formula (1) are prepared by esterificating at the 13-position the new synthones of formula (2), using suitably activated isoserine chains as acylating agents, according to what is reported in literature for the semisynthesis of taxol and its analogues) (see, for example, EP-A-400971, 1992, Fr. Dem. 86, 10400; E. Didier et al., Tetrahedron Letters 35, 2349, 1994; E. Didier at al., ibid. 35, 3063, 1994).

In formula (2)

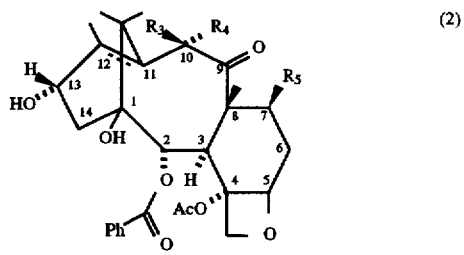

(2)

wherein:

when a double olefinic bond is present at the 11,12-position, $R_3$ is a hydrogen atom, $R_4$ and $R_5$ are hydroxy, an alkoxy group having 1 to 8 carbon atoms, $C_2$-$C_8$ acyloxy, alkylsilyloxy or 2,2,2-trichloroethoxycarbonyloxy groups;

when a double olefinic bond is not present at the 11,12-position, the methyl at the 12-position is α-oriented, $R_4$ is a hydrogen atom, $R_3$ and $R_5$ are hydroxy, an alkoxy group having 1 to 8 carbon atoms, $C_2-C_8$ acyloxy, alkylsilyloxy or 2,2,2-trichloroethoxy-carbonyloxy groups.

In particular, synthones of formula (2a) are used for the synthesis of the novel taxanes of formula (1a). On the other hand, synthones of formula (2b) are employed for the synthesis of the novel taxanes of formula (1b).

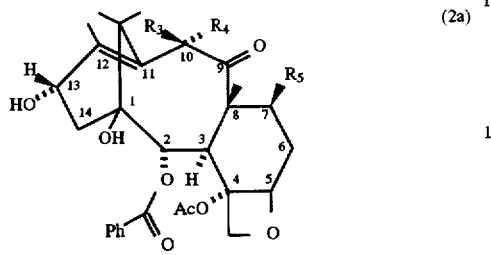
(2a)

In synthones (2a), a double olefinic bond is present at the 11,12-position, and a $C_2-C_8$ acyloxy group or an optionally protected hydroxy group are present at the 10α-position. Therefore, in synthones (2a), $R_3$ is hydrogen, $R_4$ and $R_5$ are hydroxy, acyloxy, alkylsilyloxy (such as triethylsilyloxy, O-TES) or 2,2,2-trichloroethoxycarbonyloxy (O—CO—O—CH$_2$CCl$_3$, O-TROC) groups.

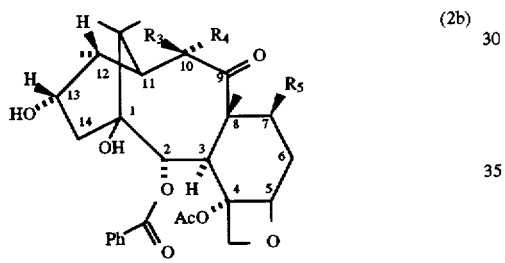
(2b)

In synthones (2b), the carbon atoms at the 11- and 12-positions are bonded by a single bond, the methyl at the 12-position is α-oriented, and an acyloxy group or an optionally protected hydroxy group are present at the 10α-position. Therefore, in synthones (2b), $R_4$ is hydrogen, $R_3$ and $R_5$ are hydroxy, acyloxy, alkylsilyloxy (such as triethylsilyloxy, O-TES) or 2,2,2-trichloroethoxycarbonyloxy (O—CO—O—CH$_2$CCl$_3$, O-TROC) groups.

After esterificating at the 13-position the synthones (2) with the isoserine chain, the protective groups are removed by conventional methods known in literature, thereby obtaining the novel taxanes of Formula (1).

10-Deacetylbaccatine III (3), which can be isolated from the leaves of Taxus Baccata (G. Chauvière et coll., C.R. Acad. Sc. Ser. III, 293; 591 [1981]), is used as the sole starting product for the preparation of synthones (2a) and (2b).

Synthones of formula (2a), which are not known in literature, are obtained (Scheme 1) from (3) by oxidation at the 10-position with copper (II) acetate, to give diketone (4), and subsequent reduction with sodium borohydride in the presence of cerium (III) salts.

The resulting product (2a, $R_3$=H, $R_4$=$R_5$=OH), which is the epimer at the 10-position of (3), is suitably protected at the 7- and 10-positions and used for the synthesis of taxanes (1a).

Scheme 1

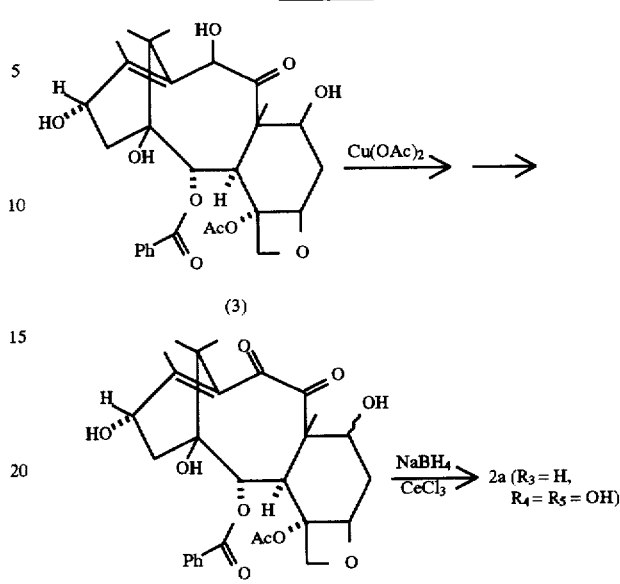

The new secotaxane (5) is obtained as a by-product of the reaction sequence given in Scheme 1

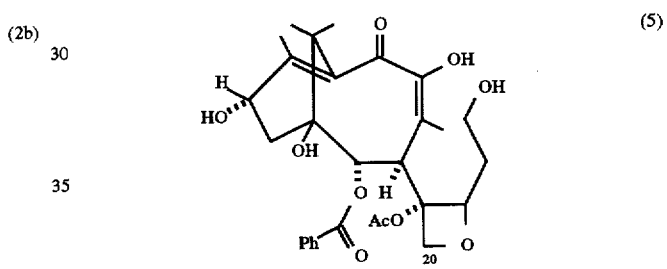
(5)

Secotaxane (5) can be used for the synthesis of further taxanes with potential anti-tumoural activity.

The present invention also relates to novel secotaxane-skeleton derivatives prepared by semisynthesis and having a powerful anti-tumoural activity. These derivatives have formula (5a)

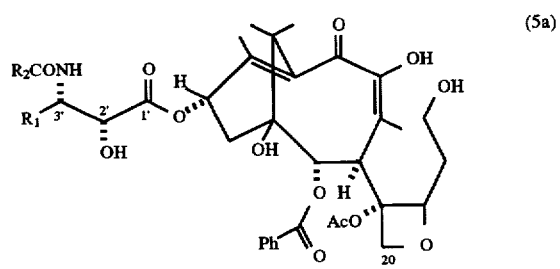
(5a)

wherein:

$R_1$ and $R_2$, which can be the same or different, are a $C_1-C_{20}$ alkyl, $C_2-C_8$ alkenyl, aryl (preferably phenyl) or heteroaryl groups. $R_2$ can also be tert-butoxy.

Taxanes of formula (5a) are prepared by esterificating compound of formula (5) in position 13, using the suitably activated isoserine chains as acylating agents, as reported in literature for the semisynthesis of taxol and analogues thereof (see for example EP-A- 400,971; E. Didier et al., Tetrahedron Letters 35, 2349, 1994; E. Didier at al., ibid. 35, 3063, 1994). The hydroxy groups of compound (5) can optionally be protected with suitable protective groups, according to conventional methods.

After the esterification of compound (5) at the 13-position with the isoserine chain, the protective groups are removed according to conventional methods known in literature, thereby obtaining secotaxanes of formula (5a).

Synthones of formula (2b), which are not known in literature, are also obtained from 10-deacetylbaccatine III (3) (Scheme 2). It has been found that by oxidation of (3) with m-chloroperbenzoic acid (MCPBA), the corresponding 13-ketoderivative (6) is obtained. After protecting the hydroxyl at the 7-position with triethylsilyl chloride (TESCl), by reduction with sodium borohydride in the presence of cerium (III) salts, (6) gives synthon (2b) ($R_3$=OH, $R_4$=H, $R_5$=O-TES), which can be useful for the synthesis of taxanes of formula (1b). The α-orientation of the methyl at the 12-position in synthones (2b) has been deduced by means of thorough studies using nuclear magnetic resonance.

Scheme 2

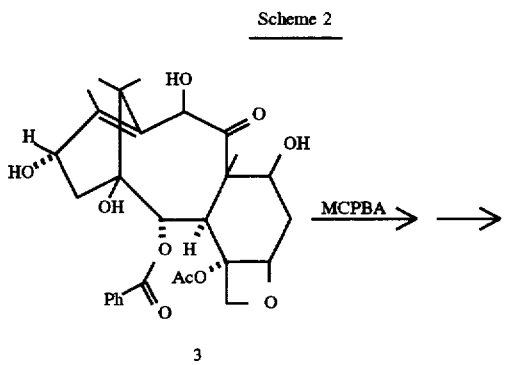

3

-continued
Scheme 2

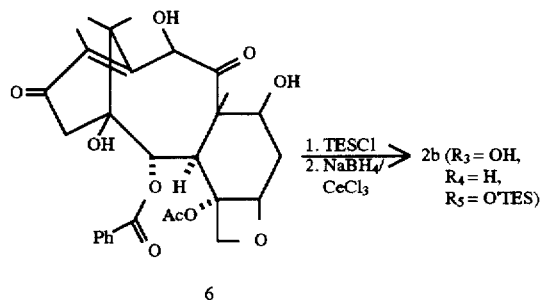

6

The products of the present invention were screened for their cytotoxic effect on different tumour cell lines, comparing their action with that of taxol. Table 1 shows the $IC_{50}$ data, compared with those found for taxol, of the compounds 13-[(2R, 3S)-3-phenyl-2-hydroxy-3-tert-butoxycarbonylamino-propanoyl]-10-epi-10-deacetylbaccatine III (1a, $R_1$=Ph, $R_2$=tBuO, $R_3$=H, $R_4$=OH), 13-[(2R, 3S)-3-phenyl-2-hydroxy-3-tert-butoxycarbonylamino-propanoyl]-10-deacetyl-11,12-dihydrobaccatine III (1b, $R_1$=Ph, $R_2$=tBuO, $R_3$=OH, $R_4$=H), 13-[(2R, 3S)-3-phenyl-2-hydroxy-3-tert-butoxy-carbonylamino-propanoyl]-C-seco-10-deacetylbaccatine III (5a, $R_1$=Ph, $R_2$=tBuO) and 13-[(2R, 3S)-3-isobutyl-2-hydroxy-3-caproylamino-propanoyl]-C-seco-10-deacetylbaccatine (5a, $R_1$=isobutyl, $R_2$=caproyl).

TABLE 1

$IC_{50}$ of taxanes 1a ($R_1$ = Ph, $R_2$ = tBuO, $R_3$ = H, $R_4$ = OH), 1b ($R_1$ = Ph, $R_2$ = tBuO, $R_3$ = H, $R_4$ = H) and of taxol on 6 cell lines.

|  | Exposure time (h) | Taxol | 1a ($R_1$ = Ph, $R_2$ = tBuO, $R_3$ = H, $R_4$ = OH) | 1b ($R_1$ = Ph, $R_2$ = tBuO, $R_3$ = H, $R_4$ = OH) |
|---|---|---|---|---|
| L1210 (murine leukemia) | 48 | 57.0 ± 3.0 | 46.0 ± 2.1 | 32.0 ± 0.1 |
| A121 (Human ovarian) | 72 | 3.7 ± 0.3 | 2.8 ± 0.3 | 1.6 ± 0.2 |
| A549 (Human NSCLC) | 72 | 5.4 ± 0.5 | 6.9 ± 0.3 | 2.1 ± 0.3 |
| HT-29 (Human colon) | 72 | 6.0 ± 0.6 | 3.4 ± 0.1 | 3.6 ± 0.4 |
| MCF7 (Human breast) | 72 | 4.3 ± 0.1 | 2.2 ± 0.2 | 0.8 ± 0.2 |
| MCF7-ADR (resistant) | 72 | 395.0 ± 8.7 | 130.0 ± 2.2 | 128.0 ± 6.2 |

$IC_{50}$ of taxanes 5a ($R_1$ = Ph, $R_2$ = tBuO), 5a ($R_1$ = isobutyl, $R_2$ = caproyl) and of taxol on 6 cell lines.

|  | Exposure time (h) | Taxol | 5a ($R_1$ = Ph, $R_2$ = tBuO) | 5b ($R_1$ = isobutyl, $R_2$ = caproyl |
|---|---|---|---|---|
| L1210 (murine leukemia) | 48 | 57.0 ± 3.0 | 35 ± 1,2 | 26 ± 1,3 |
| A121 (Human ovarian) | 72 | 3.7 ± 0.3 | 1,9 ± 0,2 | 1,3 ± 0,1 |
| A549 (Human NSCLC) | 72 | 5.4 ± 0.5 | 3,3 ± 0,4 | 2,6 ± 0,3 |
| HT-29 (Human colon) | 72 | 6.0 ± 0.6 | 3,2 ± 0,3 | 2,7 ± 0,2 |
| MCF7 (Human breast) | 72 | 4.3 ± 0.1 | 1,5 ± 0,2 | 1,1 ± 0,2 |
| MCF7-ADR (resistant) | 72 | 395.0 ± 8.7 | 31,3 ± 4,2 | 25,4 ± 3,7 |

Standard conditions: substrate RPMI 1640 + 20 mM HEPES + 2 mM L-glutamine.

Compounds with different substituents at the isoserine chain behave similarly. The compounds show surprising advantages over taxol on the cell lines resistant to other anti-tumoral substances such as adriamycin and cis-platinum. The differences between taxol and these products are still more evident in in vivo models, such as athymic nude mouse with human tumor implant. It has also been found that the compounds of the invention in which $R_2$ is an alkyl or alkenyl group are surprisingly devoid of cardiotoxic activity, unlike taxol and its known derivatives, therefore they can favourably be used in cardiopathic patients untreatable with taxol and its known derivatives.

The compounds of the invention are suited for incorporation in appropriate pharmaceutical formulations for the parenteral and oral administrations. For the intravenous administration, mixtures of polyethoxylated castor oil and ethanol, or liposomal preparations prepared with natural phosphatidyl choline or mixtures of natural phospholipids in the presence of cholesterol, are mainly used.

EXAMPLES

The examples given below further illustrate the invention.

Example 1

Preparation of 10-dehydro-10-deacetylbaccatine III (4)

10 g of 10-deacetylbaccatine III (3) are suspended in 350 ml of methanol to which 65 g of $Cu(OAc)_2$ are mixed. The suspension is continuously stirred at room temperature for 120 hours. The salts are filtered off and the solution is chromatographed on 100 g of silica gel eluting with a 6:4 hexane/ethyl acetate mixture. By crystallisation from ligroin, 9.5 g of (4) are obtained. M+at m/z 542.

Example 2

Preparation of 10-deacetyl-10-epibaccatine III (2a, $R_3$=H, $R_4$=$R_5$=OH) and C-seco-10-deacetyl-baccatine III (5)

A solution of 300 mg of (4) in 5 ml of methanol is added with one equivalent of $CeCl_3.3H_2O$, stirred at room temperature for 5 minutes, then added with 80 mg of $NaBH_4$. The solution is treated with a $NH_4Cl$ solution, extracted with ethyl acetate and chromatographed on silica gel eluting with a 3:7 hexane/ethyl acetate mixture. 98 mg of (2a) (M+at m/z 544) and 120 mg of (5) (M+at m/z 546) are obtained.

10-Deacetyl-10-epibaccatine III has the following $^1$H-NMR spectrum (CDCl$^3$): H2, d 5.68 J 6.8; H3, d 4.26 J 6.8; H5, d 5.03 J 7.1; H7/13, m 4.76; H10, br s 5.20; 10 OH, br s 3.44; H16, s 1.14; H17, s 1.68; H18, s 2.22; H19, s 1.13; H20a, d 4.33; H20b, d 4.18; Ac, s 2.31; Bnz, br 8.12 J 8, br t 7.60 J 8, br t 17.49 J 8.

Example 3

Preparation of 10-deacetyl-13-dehydrobaccatine III (6)

3 g of meta-chloroperbenzoic acid and 1 g of sodium acetate are added to a suspension of 1 g of 10-deacetylbaccatine III (3) in 100 ml of $CH_2Cl_2$. The suspension is continuously stirred for 120 hours at room temperature and then diluted with a 5% $Na_2CO_3$ aqueous solution. The organic phase is washed with 5% $Na_2CO_3$ and evaporated to dryness. The residue is purified on silica gel eluting with a 3:7 hexane/ethyl acetate mixture. 789 mg of (6), M+at m/z 542 are obtained.

Example 4

Preparation of 10-deacetyl-11,12-dihydro-7-triethylsilyl-baccatine III (2b, $R_3$=OH, $R_4$=H, $R_5$=O-TES)

1.6 g of (6) are dissolved in methylene chloride and added with 370 mg of 4-dimethylaminopyridine and 2.5 ml of triethylsilyl chloride. After 2 hours at room temperature, the reaction mixture is diluted with methylene chloride and washed with water. The organic phase is concentrated to dryness. 1.72 g of a residue is obtained, which is taken up with 150 ml of 95% ethanol and treated with 9 g of $NaBH_4$. After 3 hours the mixture is diluted with a $NH_4Cl$ solution and the product is extracted with ethyl acetate. Following chromatography on silica gel using a 7:3 hexane/ethyl acetate mixture, 800 mg of (2b) ($R_3$=OH, $R_4$=H, $R_5$=O-TES) are obtained.

Example 5

Preparation of 11,12-dihydro-7-TES-baccatine III (2b, $R_3$=OH, $R_4$=H, $R_5$=O-TES) and 11,12-dihydrobaccatine III (2b, $R_3$=OAc, $R_4$=H, $R_5$=OH)

500 mg of 10-deacetyl-11,12-dihydro-7-triethylsilylbaccatine III (2b, $R_3$=OH, $R_4$=H, $R_5$=O-TES) are reacted in anhydrous pyridine with 3 equivalents of acetyl chloride at 0° C. for 6 hours. The reaction mixture is diluted with water and extracted with methylene chloride. After evaporation of the solvent, the residue is crystallised from acetone/hexane. 510 mg of 11,12-dihydro-7-TESbaccatine III are obtained. M+ at m/z 702 III. The product is dissolved in methanol and treated with diluted HCl until complete desilylation. The reaction mixture is diluted with water, extracted with ethyl acetate and crystallisated from aqueous methanol. 400 mg of 11,12-dihydrobaccatine III are obtained. M+at m/z 588.

Example 6

Preparation of 13-[(2R, 3S)-3-phenyl-2-hydroxy-3-tert-butoxycarbonylamino-propanoyl]-11,12-dihydrobaccatine III (1b, $R_1$=Ph, $R_2$=tBuO, $R_3$=OAc, $R_4$=H)

500 mg of 11,12-dihydrobaccatine III (2b, $R_3$=OAc, $R_4$=H, $R_5$=O-TES) are dissolved in 20 ml of toluene with 0.45 g of (4S, 5R)-N-tert-butoxycarbonyl-2,2-dimethylphenyl-5-oxazolydinecarboxylic acid, dicyclohexylcarbodiimide (1.03 eq) and N,N-dimethylaminopyridine (0.2 eq) at 80° C. for 2 hours. The reaction mixture is washed with water until the excess of the reagents is removed, then concentrated to dryness. The residue is treated with methanol containing 1% formic acid for 4 hours at room temperature. The methanol solution is diluted with water, neutralised and extracted with ethyl acetate. The organic phase is concentrated to dryness and the residue is treated with a solution containing 1.5 eq of di-tert-butyl carbonate and sodium bicarbonate in 15 ml of tetrahydrofuran. The reaction mixture is diluted with water, extracted with ethyl acetate and the heteroacetic phase is concentrated to dryness. The residue is taken up with acidic methanol by hydrochloric acid to complete desilylation. The solution is then diluted with water and extracted with ethyl acetate. The residue obtained by evaporation of the heteroacetic phase is chromatographed on silica gel eluting with a 1:1 acetone/hexane mixture to remove the reaction impurities. 580 mg of product are obtained, M+ at m/z 851.

Example 7

Preparation of 13-[(2R, 3S)-3-benzoylamino-3-phenyl-2-hydroxypropanoyl]-11,12-dihydrobaccatine III (1b, $R_1=R_2=Ph$, $R_3=OAc$, $R_4=H$).

500 mg of 11,12-dihydro-7-TES-baccatine (2b, $R_3=OAc$, $R_4=H$, $R_5=O-TES$) are dissolved in 20 ml of toluene together with 1.5 g of (4S, 5R)-N-benzoyl-2,2-dimethyl-4-phenyl-5-oxazolydinecarboxylic acid, dicyclohexylcarbodiimide (1.03 eq) and N,N-dimethylaminopyridine (0.2 eq) at 80° C. for 2 hours. The reaction mixture is washed with water until the excess of reagents is removed, then concentrated to dryness. The residue is treated with methanol containing 1% formic acid for 4 hours at room temperature. The methanol solution is diluted with water, neutralised and extracted with ethyl acetate. The organic phase is concentrated to dryness and the residue is taken up with methanol acidic by hydrochloric acid to complete desilylation. The solution is then diluted with water and extracted with ethyl acetate. The residue obtained by evaporation of the heteroacetic phase is chromatographed on silica gel eluting with a 1:1 acetone/hexane mixture to remove the reaction impurities. 530 mg of product are obtained, M+ at m/z 855.

Example 8

Preparation of 13-[(2R, 3S)-3-phenyl-2-hydroxy-3-tert-butoxycarbonylamino-propanoyl]-10-epi-10-deacetylbaccatine III (1a, $R_1=Ph$, $R_2=tBuO$, $R_3=H$, $R_4=OH$)

500 mg of 10-deacetyl-10-epibaccatine III (2a, $R_3=H$, $R_4=R_5=OH$) are dissolved in 15 ml of anhydrous pyridine and treated for 5 minutes at 80° C. with three equivalents of trichloroethoxycarbonyl chloride (TROC-Cl) and then cooled to room temperature. 1 ml of methanol is added to decompose the excess TROC-CL. The solution is diluted with iced water and extracted with chloroform, washing the organic phase with a hydrochloric acid diluted solution. The organic phase is evaporated to dryness and the residue is treated at room temperature for 24 hours with a toluene solution containing three equivalents of (4S, 5R)-N-tert-butoxycarbonyl-2,2-dimethyl-4-phenyl-5-oxazolydinecarboxylic acid, 3 equivalents of dicyclohexylcarbodiimide and 0.2 equivalents of N,N-dimethylaminopyridine. The reaction mixture is washed with water and the organic phase is evaporated to dryness under vacuum. The residue is taken up with methanol and treated with one equivalent of p-toluenesulfonic acid for 48 hours, after that is diluted with water and extracted with ethyl acetate. The organic phase is evaporated under vacuum and the residue is taken up in 200 ml of a 1:1 acetic acid/ethyl acetate mixture and treated for 3 hours at 30° C. with 11 equivalents of powdered zinc. The solid material is filtered off and the solution is diluted with water, extracted with ethyl acetate and chromatographed on silica gel eluting with a 1:4 ethyl acetate/hexane mixture. 512 mg of product (1a) are obtained, M+ at m/z 807.

Example 9

Preparation of 7,9-ditriethylsilyl-C-seco-10-deacetylbaccatine III

A solution of (5) (200 mg, 0.37 mmol) in anhydrous dimethylformamide (DMF) (5 ml), is added with imidazole (75 mg, 1.11 mmol, 3 eq. mol) and triethylsilyl chloride (TES) (186 ml, 167.3 mg, 1.11 mmol, 3 eq. mol) and the reaction mixture is stirred for 10 minutes at room temperature. The reaction is checked by TLC (3:7 hexane-ethyl acetate, Rf of the starting material 0.10, Rf of the product 0.80). The reaction is quenched by addition of water and Celite$^R$, and the precipitate is filtered and washed with water to remove DMF, then with $CHCl_3$ to remove the product. After purification by column chromatography (9:1 hexane/ethyl acetate to elute silanol, then 6:4 hexane/ethyl acetate to elute the product) 146 mg of the title product are obtained (51%).

Example 10

Preparation of 13-[(2R,3S)-3-phenyl-2-hydroxy-3-tert-butoxycarbonylamino-propanoyl-C-seco-10-deacetylbaccatine III (5a, $R_1=Ph$, $R_2=tBuO$)

A solution of the product obtained in example 9 (126 mg, 0.16 mmol) in anhydrous toluene (5 ml), is added with 67.5 mg of dicyclohexylcarbodiimide (0.327 mmol, 2 mol. eq.), 105 mg of (4S,5R)-N-Boc-2-(2,4-dimethoxyphenyl)-4-phenyl-5-oxazolidinecarboxylic (0.327 mmol, 2 mol eq.) and 5 mg of 4-dimethylaminopyridine. The mixture is heated to 60° C. for 24 hours and diluted with a $NaHCO_3$ saturated aqueous solution and ethyl acetate. The residue is purified by column chromatography (8:2 hexane-ethyl acetate) to give 175 mg of the 13-ester (95%). The residue is taken up with 50 ml of methanol/HCl (0.01%) and the reaction mixture is left at room temperature for 1 hour. The solution is alkalinized to pH 5 and concentrated to dryness under vacuum. The residue is chromatographed on a silica gel column eluting with a 98:2 methylene chloride-methanol mixture. After crystallization from ethyl acetate, 85 mg of the title compound are obtained.

Example 11

Preparation of 13-[(2R,3S)-3-isobutyl-2-hydroxy-3-caproylamino-propanoyl-C-seco-10-deacetylbaccatine III (5a, $R_1=Ph$, $R_2=caproyl$)

A solution of the product obtained in example 9 (126 mg, 0.16 mmol) in anhydrous toluene (5 ml), is added with 67.5 mg of dicyclohexylcarbodiimide (0.327 mmol, 2 mol. eq.), 140 mg of (4S,5R)-N-caproyl-2-(2,4-dimethoxyphenyl)-4-isobutyl-5-oxazolidinecarboxylic acid (0,327 mmol, 2 mol eq.) and 5 mg of 4-dimethylaminopyridine. The mixture is heated to 60° C. for 24 hours and diluted with a $NaHCO_3$ saturated aqueous solution and ethyl acetate. The residue is purified by column chromatography (8:2 hexane-ethyl acetate) to give 175 mg of the 13-ester (95%). The residue is taken up with 50 ml of methanol/HCl (0.01%) and the reaction mixture is left at room temperature for 1 hour. The solution is alkalinized to pH 5 and concentrated to dryness under vacuum. The residue is chromatographed on a silica gel column eluting with a 98:2 methylene chloride-methanol mixture. After crystallization from ethyl acetate, 88 mg of the title compound are obtained.

We claim:

1. 13-[(2R, 3S)-3-phenyl-2-hydroxy-3-tert-butoxycarbonylamino-propanoyl]-11,12-dihydrobaccatine III, of formula (1b)

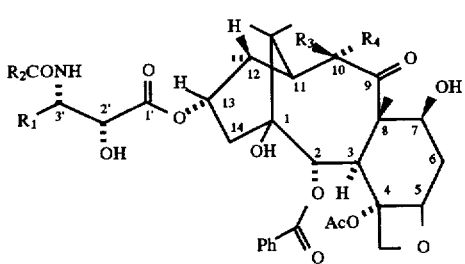

where $R_1$ is phenyl, $R_2$ is tert-butoxy, $R_3$ is acetoxy and $R_4$ is H.

2. As an intermediate, a compound of formula (5)

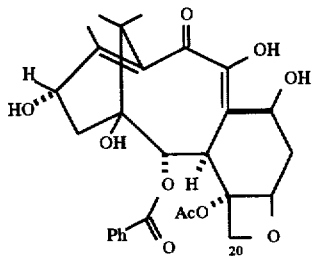

3. A semisynthetic secotaxane of formula 5a

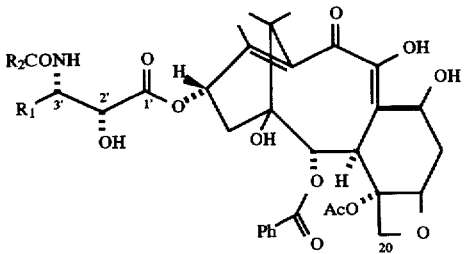

wherein:

$R_1$ and $R_2$, which can be the same or different, are a $C_1$–$C_{20}$ alkyl, $C_2$–$C_8$ alkenyl, aryl or heteroaryl group. $R_2$ can also be an alkoxy group having 1 to 8 carbon atoms.

4. As compound according to claim 3, 13-[(2R,3S)-3-phenyl-2-hydroxy-3-tert-butoxycarbonylamino-propanoyl]-C-seco-10-deacetylbaccatine III, of formula 5a

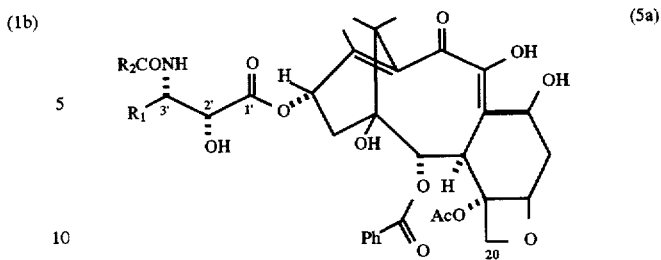

wherein $R_1$ is phenyl, $R_2$ is tert-butoxy.

5. As compound according to the claim 3, 13-[(2R,3S)-3-isobutyl-2-hydroxy-3-caproylamino-propanoyl-C-seco-10-deacetylbaccatine III of formula 5a wherein $R_1$ is isobutyl, $R_2$ is caproyl.

6. A process for the preparation of the compounds according to claim 3, wherein compound of formula 5

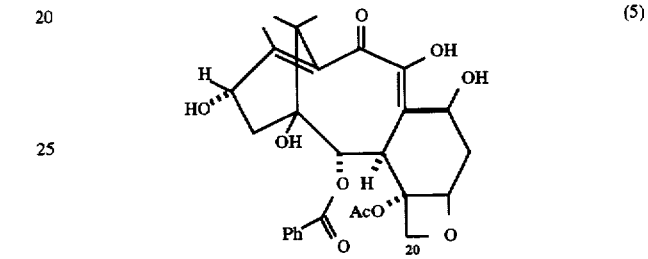

is subjected to esterification with derivatives suitably activated and/or protected at the isoserine chain, thereby introducing the acyl group in the 13-position

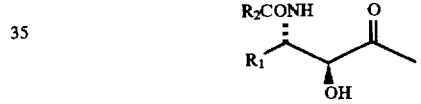

(wherein $R_1$ and $R_2$ have the meanings defined in claim 3), thereafter removing the protective groups.

7. Pharmaceutical compositions containing taxanes according to claim 1.

8. A method of treatment of a tumor in a cardiopathic patent, which comprises administering to the patent a therapeutically effective amount of a taxane compound according to claim 1.

* * * * *

UNITED STATES PATENT AND TRADEMARK OFFICE
CERTIFICATE OF CORRECTION

PATENT NO. : 5,756,776                                    Page 1 of 1
DATED     : May 26, 1998
INVENTOR(S) : Ezio Bombardelli et al.

It is certified that error appears in the above-identified patent and that said Letters Patent is hereby corrected as shown below:

Columns 11 and 12, replace the figure in claims 2 and 6 as follows:

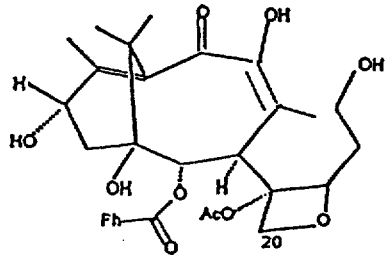

Columns 11 and 12, replace the figure in claims 3 and 4 as follows:

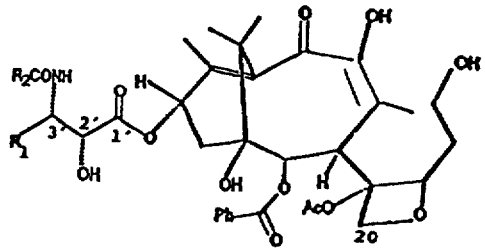

Claim 8, line 45, please change: "patent" to --patient--.

Signed and Sealed this

Seventh Day of August, 2001

*Attest:*

NICHOLAS P. GODICI
*Attesting Officer*    Acting Director of the United States Patent and Trademark Office